US00PP11803P2

(12) United States Plant Patent
Bartels

(10) Patent No.: US PP11,803 P2
(45) Date of Patent: Mar. 13, 2001

(54) PHLOX PLANT NAMED 'BARNINE'

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 0 days.

(21) Appl. No.: 09/328,637

(22) Filed: Jun. 9, 1999

(51) Int. Cl.[7] ..... A01H 5/00

(52) U.S. Cl. ..... Plt./320

(58) Field of Search ..... Plt./320

(56) References Cited

PUBLICATIONS

UPOV ROM GTITM Computer Database 2000/4, GTI JOAVE Retrieval Softward, citations for 'Barnine', Aug. 2000.*

* cited by examiner

*Primary Examiner*—Bruce R. Campell
*Assistant Examiner*—Wendy A. Baker
(74) *Attorney, Agent, or Firm*—C. A. Whealy

(57) ABSTRACT

A distinct cultivar of Phlox plant named 'Barnine', characterized by its upright plant habit; relatively fast growth rate; dark green foliage color; attractive dark pink flowers with reddish purple throat; and excellent postproduction longevity.

1 Drawing Sheet

BACKGROUND OF THE INVENTION

The present invention relates to a new and distinct cultivar a of Phlox plant, botanically known as 'Phlox paniculata', and hereinafter referred to by the cultivar name Barnine.

The new Phlox is a product of a planned breeding program conducted by the Inventor in Aalsmeer, The Netherlands. The objective of the breeding program was to create new Phlox cultivars having desirable cut flower characteristics.

The new Phlox originated from a cross made by the Inventor of two proprietary Phlox seedling selections identified as code number 90.44.06.01 as the female, or seed, parent and 90.44.12.03 as the male, or pollen, parent. The cultivar Barnine was discovered and selected by the Inventor as a flowering plant within the progeny of the stated cross in a controlled environment in Aalsmeer, The Netherlands, in 1994.

Asexual reproduction of the new cultivar by terminal cuttings taken at Aalsmeer, The Netherlands, has shown that the unique features of this new Phlox are stable and reproduced true to type in successive generations.

SUMMARY OF THE INVENTION

Plants of the cultivar Barnine have not been observed under all possible environmental conditions. The phenotype may vary somewhat with variations in environment such as temperature, light intensity, daylength, and fertility level without, however, and variance in genotype.

The following traits have been repeatedly observed and are determined to be the unique characteristics of 'Barnine'. These characteristics in combination distinguish 'Barnine' as a new and distinct cultivar:

1. Upright plant habit.
2. Relatively fast growth rate.
3. Dark green foliage color.
4. Attractive dark pink flowers with reddish purple throat.
5. Excellent postproduction longevity.

BRIEF DESCRIPTION OF THE PHOTOGRAPH

The accompanying colored photograph illustrates the overall appearance of the new cultivar, showing the colors as true as it is reasonably possible to obtain in colored reproductions of this type.

The photograph comprises a close-up view of a typical flowering panicle of the new Phlox. Flower colors in the photograph may appear different than the actual colors due to light reflectance.

DETAILED BOTANICAL DESCRIPTION

In the following description, color references are made to The Royal Horticultural Society Colour Chart except where general terms of ordinary dictionary significance are used.

Plants used for the description were grown under outdoor production conditions with average day and night temperatures of about 16 and 14° C., respectively, in Aalsmeer, The Netherlands. Plants used for the description were about 12 weeks old.

Botanical classification: *Phlox paniculata* cultivar Barnine.

Parentage:

*Female parent*.—Proprietary *Phlox paniculata* selection identified as 90.44.06.01, not patented.

*Male parent*.—Proprietary *Phlox paniculata* selection identified as 99.44.12.03, not patented.

Propagation:

*Type*.—By cuttings.

*Time to initiate roots*.—Summer: About 21 days at 18° C. Winter: About 35 days at 18° C.

*Time to develop roots* (*time to produce a rooted liner*) .—Summer: About 28 days at 18° C. Winter: About 42 days at 18° C.

*Root description*.—Thick in diameter.

Plant description:

*Crop time*.—From cuttings, about 12 weeks are required to produce a flowering plant with harvestable cut flowers.

*Form*.—Strong, upright and tall perennial herb. Typically grown for cut flower production.

*Plant height*.—About 100 cm.

*Plant width*.—About 25 cm.

*Vigor*.—Moderate, growth rate.

*Lateral branches*.—Quantity: Pinching enhances lateral branch development; typically four per plant. Length: 100 cm. Width: 8 cm. Color: 145A. Internode length: About 5 cm. Texture: Glabrous.

*Foliage description*.—Leaves simple, opposite, generally symmetrical, and long persisting. Tolerant to stresses. Quantity per lateral branch: Typically about 30. Length: About 8 cm. Width: About 4 cm. Shape: Oblong/elliptic. Apex: Sharply acute. Base: Rounded. Margin: Entire. Texture: Leathery. Color: Young foliage, upper surface: 147A. Young foliage, lower surface: 137A. Mature foliage, upper surface: 147A. Mature foliage, lower surface: 137A. Venation, upper surface: 137A. Venation, lower surface: 137A.

Flower description:

*Flower type and habit*.—Single round flowers arranged in terminal panicles, one per stem; flowers face upright. Panicles pyramidal in shape. Freely flowering. Corolla, salverform, 5-lobed; calyx five-cleft. Flowers last about four days on the plant. Not persistent.

*Natural flowering season*.—Continuously flowering from July through September.

*Quantity*.—Very freely flowering with numerous flowers per panicle.

*Fragrance*.—Present; typical of species.

*Flower buds*.—Length: About 1 cm. Diameter: About 5 mm. Shape: Elliptic. Color: 144A. Rate of opening: About one day.

*Flowers size*.—About 2 cm.

*Petals*.—Quantity: Five, fused. Length: About 2.5 cm. Width: About 1 cm. Shape: Broadly ovate. Apex: Rounded. Margin: Entire. Surface: Typically flat. Texture: Smooth. Color: Upper and lower surfaces, when opening and fully opened: Dark pink, 68A; fading to 68B. Base of petals, flower throat (inside) and flower tube (outside), fully opened: Reddish purple, 67A.

*Calyx*.—Shape: Campanulate; sepals, linear, fused at base. Sepal quantity: Five. Sepal apex: Acuminate. Sepal margin: Entire. Texture: Smooth. Color, upper and lower surfaces: 144A.

*Pedicel*.—Strength: Strong. Angle: About 45° to peduncle. Length: About 1 cm. Color: 145A.

*Reproductive organs*.—Pollen: Scarce. Pollen color: 2D. Pistil length: About 2.5 cm. Stigma shape: Trilobed. Stigma color: 154D. Style length: About 2.5 cm. Style color: 154D. Ovary color: 144A.

*Seed development*.—Seed development has not been observed.

Disease tolerance: Under commercial conditions, tolerance to Powdery Mildew has been observed.

It is claimed:

1. A new and distinct cultivar of Phlox plant named 'Barnine', as illustrated and described.

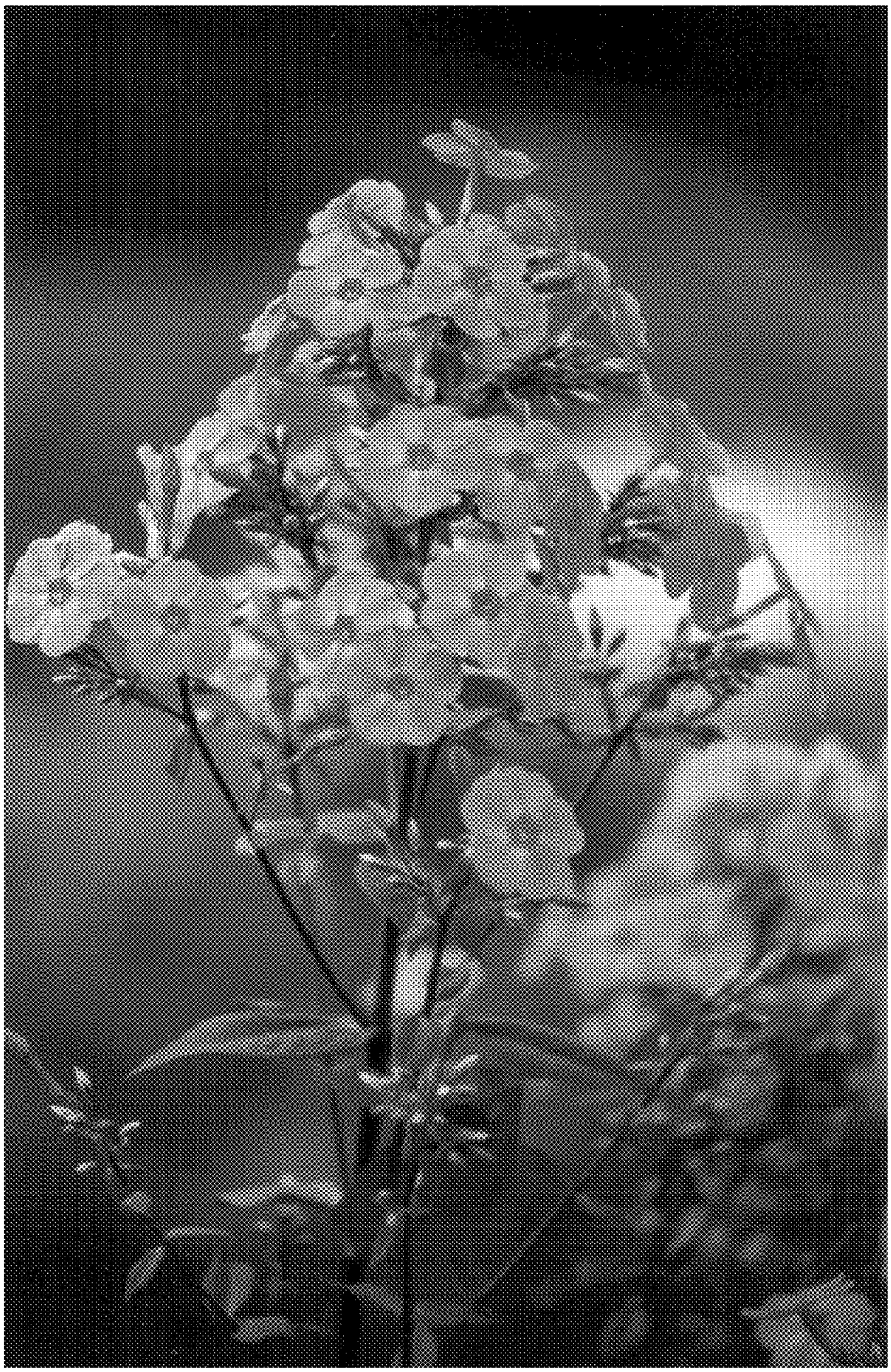

* * * * *